(12) United States Patent
Kaifosh et al.

(10) Patent No.: US 11,000,211 B2
(45) Date of Patent: May 11, 2021

(54) ADAPTIVE SYSTEM FOR DERIVING CONTROL SIGNALS FROM MEASUREMENTS OF NEUROMUSCULAR ACTIVITY

(71) Applicant: Facebook Technologies, LLC, Menlo Park, CA (US)

(72) Inventors: Patrick Kaifosh, New York, NY (US); Timothy Machado, Palo Alto, CA (US); Thomas Reardon, New York, NY (US); Erik Schomburg, Brooklyn, NY (US); Joshua Merel, London (GB); Steven Demers, Manchester, NH (US)

(73) Assignee: Facebook Technologies, LLC, Menlo Park, CA (US)

( * ) Notice: Subject to any disclaimer, the term of this patent is extended or adjusted under 35 U.S.C. 154(b) by 851 days.

(21) Appl. No.: 15/659,487

(22) Filed: Jul. 25, 2017

(65) Prior Publication Data

US 2018/0020951 A1 Jan. 25, 2018

Related U.S. Application Data

(60) Provisional application No. 62/366,427, filed on Jul. 25, 2016.

(51) Int. Cl.
*A61B 5/11* (2006.01)
*A61F 2/72* (2006.01)
(Continued)

(52) U.S. Cl.
CPC ............ *A61B 5/1106* (2013.01); *A61B 5/316* (2021.01); *A61B 5/378* (2021.01); *A61B 5/389* (2021.01);
(Continued)

(58) Field of Classification Search
CPC . A61B 5/1106; A61B 5/0488; A61B 5/04012; A61B 5/04842; A61B 5/681;
(Continued)

(56) References Cited

U.S. PATENT DOCUMENTS 4,055,168 A 10/1977 Miller et al.
4,896,120 A 1/1990 Kamil
(Continued)

FOREIGN PATENT DOCUMENTS

CA 2902045 A1 8/2014
CA 2921954 A1 2/2015
(Continued)

OTHER PUBLICATIONS encylopedia.com definition of autoregressive models (Year: 2020).*
(Continued)

*Primary Examiner* — Jacqueline Cheng
*Assistant Examiner* — Tho Q Tran
(74) *Attorney, Agent, or Firm* — FisherBroyles, LLP

(57) ABSTRACT

Methods and apparatus for adapting a control mapping associating sensor signals with control signals for controlling an operation of a device. The method comprises obtaining first state information for an operation of the device, providing the first state information as input to an intention model associated with an operation of the device and obtaining corresponding first intention model output, providing a plurality of neuromuscular signals recorded from a user and/or signals derived from the neuromuscular signals as inputs to a first control mapping and obtaining corresponding first control mapping output, and updating the first control mapping using the inputs provided to the first control mapping and the first intention model output to obtain a second control mapping.

20 Claims, 7 Drawing Sheets

(51) Int. Cl.
   *A61B 5/316*  (2021.01)
   *A61B 5/389*  (2021.01)
   *A61B 5/00*   (2006.01)
   *A61B 5/30*   (2021.01)
   *A61B 5/296*  (2021.01)
   *A61B 5/378*  (2021.01)
   *A61B 5/38*   (2021.01)

(52) U.S. Cl.
   CPC ............... *A61B 5/681* (2013.01); *A61F 2/72* (2013.01); *A61B 5/296* (2021.01); *A61B 5/30* (2021.01); *A61B 5/38* (2021.01)

(58) Field of Classification Search
   CPC .............. A61B 5/04888; A61B 5/0492; A61B 5/04004; A61B 5/04845
   See application file for complete search history.

(56) References Cited

U.S. PATENT DOCUMENTS

| | | |
|---|---|---|
| 5,625,577 A | 4/1997 | Kunii et al. |
| 6,005,548 A | 12/1999 | Latypov et al. |
| 6,009,210 A | 12/1999 | Kand |
| 6,244,873 B1 | 6/2001 | Hill et al. |
| 6,411,843 B1 | 6/2002 | Zarychta |
| 6,658,287 B1 | 12/2003 | Litt et al. |
| 6,720,984 B1 | 4/2004 | Jorgensen et al. |
| 6,774,885 B1 | 8/2004 | Even-Zohar |
| 6,942,621 B2 | 9/2005 | Avinash et al. |
| 7,089,148 B1 | 8/2006 | Bachmann et al. |
| 7,351,975 B2 | 4/2008 | Brady et al. |
| 7,574,253 B2 | 8/2009 | Edney et al. |
| 7,580,742 B2 | 8/2009 | Tan et al. |
| 7,787,946 B2 | 8/2010 | Stahmann et al. |
| 7,805,386 B2 | 9/2010 | Greer |
| 7,901,368 B2 | 3/2011 | Flaherty et al. |
| 8,170,656 B2 | 5/2012 | Tan et al. |
| 8,190,249 B1 | 5/2012 | Gharieb et al. |
| 8,311,623 B2 | 11/2012 | Sanger |
| 8,351,651 B2 | 1/2013 | Lee |
| 8,421,634 B2 | 4/2013 | Tan et al. |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,484,022 B1 | 7/2013 | Vanhoucke |
| 8,718,980 B2 | 5/2014 | Garudadri et al. |
| 8,744,543 B2 | 6/2014 | Li et al. |
| 8,754,862 B2 | 6/2014 | Zaliva |
| D717,685 S | 11/2014 | Bailey et al. |
| 8,880,163 B2 | 11/2014 | Barachant et al. |
| 8,890,875 B2 | 11/2014 | Jammes et al. |
| 8,892,479 B2 | 11/2014 | Tan et al. |
| 9,037,530 B2 | 5/2015 | Tan et al. |
| D742,272 S | 11/2015 | Bailey et al. |
| 9,218,574 B2 | 12/2015 | Phillipps et al. |
| 9,235,934 B2 | 1/2016 | Mandella et al. |
| 9,240,069 B1 | 1/2016 | Li |
| 9,278,453 B2 | 3/2016 | Assad |
| 9,299,248 B2 | 3/2016 | Lake et al. |
| D756,359 S | 5/2016 | Bailey et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,459,697 B2 | 10/2016 | Bedikian et al. |
| 9,483,123 B2 | 11/2016 | Aleem et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,460,455 B2 | 10/2019 | Giurgica-Tiron et al. |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0092839 A1 | 5/2004 | Shin et al. |
| 2007/0009151 A1 | 1/2007 | Pittman et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0009771 A1* | 1/2008 | Perry ................... B25J 9/0006 600/587 |
| 2008/0052643 A1 | 2/2008 | Ike et al. |
| 2008/0214360 A1 | 9/2008 | Stirling et al. |
| 2008/0221487 A1 | 9/2008 | Zohar et al. |
| 2009/0082692 A1 | 3/2009 | Hale et al. |
| 2009/0082701 A1 | 3/2009 | Zohar et al. |
| 2009/0112080 A1 | 4/2009 | Matthews |
| 2009/0124881 A1 | 5/2009 | Rytky |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0063794 A1 | 3/2010 | Hernandez-Rebollar |
| 2010/0106044 A1* | 4/2010 | Linderman ............ A61B 5/411 600/546 |
| 2010/0113910 A1 | 5/2010 | Brauers et al. |
| 2010/0280628 A1 | 11/2010 | Sankai |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2011/0077484 A1 | 3/2011 | Van Slyke et al. |
| 2011/0092826 A1 | 4/2011 | Lee et al. |
| 2011/0173204 A1 | 7/2011 | Murillo et al. |
| 2012/0066163 A1 | 3/2012 | Balls et al. |
| 2012/0188158 A1 | 7/2012 | Tan et al. |
| 2012/0265480 A1 | 10/2012 | Oshima |
| 2012/0283526 A1 | 11/2012 | Gommesen et al. |
| 2013/0004033 A1 | 1/2013 | Trugenberger |
| 2013/0077820 A1 | 3/2013 | Marais et al. |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1* | 8/2014 | Lake .................... G06F 3/017 340/12.5 |
| 2014/0240223 A1 | 8/2014 | Lake et al. |
| 2014/0245200 A1 | 8/2014 | Holz |

(56) References Cited

U.S. PATENT DOCUMENTS

| | | |
|---|---|---|
| 2014/0249397 A1 | 9/2014 | Lake et al. |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0334083 A1 | 11/2014 | Bailey |
| 2014/0344731 A1 | 11/2014 | Holz |
| 2014/0355825 A1 | 12/2014 | Kim et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0292497 A1 | 10/2016 | Kehtarnavaz et al. |
| 2016/0313798 A1 | 10/2016 | Connor |
| 2016/0313801 A1* | 10/2016 | Wagner .................. G09B 21/02 |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0340506 A1* | 11/2017 | Zhang .................... A61H 1/024 |
| 2018/0000367 A1 | 1/2018 | Longinotti-Buitoni |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0088765 A1 | 3/2018 | Bailey |
| 2018/0095630 A1 | 4/2018 | Bailey |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |

FOREIGN PATENT DOCUMENTS

| | | |
|---|---|---|
| CA | 2939644 A1 | 8/2015 |
| CN | 1838933 A | 9/2006 |
| CN | 105190578 A | 12/2015 |
| CN | 106102504 A | 11/2016 |
| CN | 110312471 A | 10/2019 |
| EP | 2198521 B1 | 6/2012 |
| EP | 2959394 A1 | 12/2015 |
| EP | 3104737 A1 | 12/2016 |
| EP | 3 487 457 A1 | 5/2019 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | 2008/022435 A1 | 2/2008 |
| WO | WO 2008/109248 A2 | 9/2008 |
| WO | WO 2009/042313 A1 | 4/2009 |
| WO | WO 2010/104879 A2 | 9/2010 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |

(56) References Cited

FOREIGN PATENT DOCUMENTS

| WO | WO 2017/120669 A1 | 7/2017 |
|---|---|---|
| WO | WO 2017/172185 A1 | 10/2017 |
| WO | 2018/022658 A1 | 2/2018 |

OTHER PUBLICATIONS

PCT/US2017/043686, Oct. 6, 2017, International Search Report and Written Opinion.
PCT/US2017/043686, Feb. 7, 2019, International Preliminary Report on Patentability.
PCT/US2017/043693, Oct. 6, 2017, International Search Report and Written Opinion.
PCT/US2017/043693, Feb. 7, 2019, International Preliminary Report on Patentability.
PCT/US2017/043791, Oct. 5, 2017, International Search Report and Written Opinion.
PCT/US2017/043791, Feb. 7, 2019, International Preliminary Report on Patentability.
PCT/US2017/043792, Oct. 5, 2017, International Search Report and Written Opinion.
PCT/US2017/043792, Feb. 7, 2019, International Preliminary Report on Patentability.
PCT/US2018/056768, Jan. 15, 2019, International Search Report and Written Opinion.
PCT/US2018/061409, Mar. 12, 2019, International Search Report and Written Opinion.
International Search Report and Written Opinion for International Application No. PCT/US2017/043686 dated Oct. 6, 2017.
International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
Benko et al., Enhancing Input On and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Li et al., Motor Function Evaluation of Hemiplegic Upper-Extremities Using Data Fusion from Wearable Inertial and Surface EMG Sensors. Sensors. MDPI. 2017;17(582):1-17.
McIntee, A Task Model of Free-Space Movement-Based Geastures. Dissertation. Graduate Faculty of North Carolina State University. Computer Science. 2016. 129 pages.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
International Search Report and Written Opinion for International Application No. PCT/US2019/028299 dated Aug. 9, 2019.
Invitation to Pay Additional Fees for International Application No. PCT/US2019/031114 dated Aug. 6, 2019.
International Search Report and Written Opinion for International Application No. PCT/US2019/034173 dated Sep. 18, 2019.
International Search Report and Written Opinion for International Application No. PCT/US2019/037302 dated Oct. 11, 2019.
Invitation to Pay Additional Fees for International Application No. PCT/US2019/049094 dated Oct. 24, 2019.
Gopura et al., A Human Forearm and wrist motion assist exoskeleton robot with EMG-based fuzzy-neuro control. Proceedings of the

(56) References Cited

OTHER PUBLICATIONS

2nd IEEE/RAS-EMBS International Conference on Biomedical Robotics and Biomechatronics. Oct. 19-22, 2008. 6 pages.

Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].

Valero-Cuevas et al., Computational Models for Neuromuscular Function. NIH Public Access Author Manuscript. Jun. 16, 2011. 52 pages.

Yang et al., Surface EMG based handgrip force predictions using gene expression programming. Neurocomputing. 2016;207:568-579.

International Search Report and Written Opinion for International Application No. PCT/US2018/063215 dated Mar. 21, 2019.

International Search Report and Written Opinion for International Application No. PCT/US2019/015134 dated May 15, 2019.

International Search Report and Written Opinion for International Application No. PCT/US2019/015167 dated May 21, 2019.

International Search Report and Written Opinion for International Application No. PCT/US2019/015174 dated May 21, 2019.

International Search Report and Written Opinion for International Application No. PCT/US2019/015238 dated May 16, 2019.

International Search Report and Written Opinion for International Application No. PCT/US2019/015183 dated May 3, 2019.

International Search Report and Written Opinion for International Application No. PCT/US2019/015180 dated May 28, 2019.

International Search Report and Written Opinion for International Application No. PCT/US2019/015244 dated May 16, 2019.

International Search Report and Written Opinion for International Application No. PCT/US19/20065 dated May 16, 2019.

Arkenbout et al., Robust Hand Motion Tracking through Data Fusion of 5DT Data Glove and Nimble VR Kinect Camera Measurements. Sensors. 2015;15:31644-71.

Davoodi et al., Development of a Physics-Based Target Shooting Game to Train Amputee Users of Multijoint Upper Limb Prostheses. Presence. Massachusetts Institute of Technology. 2012;21(1):85-95.

Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.

Hauschild et al., A Virtual Reality Environment for Designing and Fitting Neural Prosthetic Limbs. IEEE Transactions on Neural Systems and Rehabilitation Engineering. 2007;15(1):9-15.

Lee et al., Motion and Force Estimation System of Human Fingers. Journal of Institute of Control, Robotics and Systems. 2011;17(10):1014-1020.

Lopes et al., Hand/arm gesture segmentation by motion using IMU and EMG sensing. ScienceDirect. Elsevier. Procedia Manufacturing. 2017;11:107-13.

Martin et al., A Novel Approach of Prosthetic Arm Control using Computer Vision, Biosignals, and Motion Capture. IEEE. 2014. 5 pages.

Mendes et al., Sensor Fusion and Smart Sensor in Sports and Biomedical Applications. Sensors. 2016;16(1569):1-31.

Sartori et al., Neural Data-Driven Musculoskeletal Modeling for Personalized Neurorehabilitation Technologies. IEEE Transactions on Biomedical Engineering. 2016;63(5):879-93.

PCT/US2019/028299, Aug. 9, 2019, International Search Report and Written Opinion.

PCT/US2019/031114, Aug. 6, 2019, Invitation to Pay Additional Fees.

PCT/US2019/034173, Sep. 18, 2019 International Search Report and Written Opinion.

PCT/US2019/037302, Oct. 11, 2019, International Search Report and Written Opinion.

PCT/US2019/049094, Oct. 24, 2019, Invitation to Pay Additional Fees.

PCT/US2018/063215, Mar. 21, 2019, International Search Report and Written Opinion.

PCT/US2019/015134, May 15, 2019, International Search Report and Written Opinion.

PCT/US2019/015167, May 21, 2019, International Search Report and Written Opinion.

PCT/US2019/015174, May 21, 2019, International Search Report and Written Opinion.

PCT/US2019/015238, May 16, 2019, International Search Report and Written Opinion.

PCT/US2019/015183, May 3, 2019, International Search Report and Written Opinion.

PCT/US2019/015180, May 28, 2019, International Search Report and Written Opinion.

PCT/US2019/015244, May 16, 2019, International Search Report and Written Opinion.

PCT/US19/20065, May 16, 2019, International Search Report and Written Opinion.

Extended European Search Report received for EP Patent Application Serial No. 17835141.7 dated Jul. 15, 2020, 8 pages.

\* cited by examiner

ADAPTIVE SYSTEM FOR DERIVING CONTROL SIGNALS FROM MEASUREMENTS OF NEUROMUSCULAR ACTIVITY

CROSS-REFERENCE TO RELATED APPLICATIONS

This application claims the benefit under 35 U.S.C. § 119(e) of U.S. Provisional Patent Application Ser. No. 62/366,427, filed Jul. 25, 2016, and entitled "ADAPTIVE SYSTEM FOR DERIVING CONTROL SIGNALS FROM MEASUREMENTS OF MUSCLE OR MOTOR UNIT ACTIVITY," the entire contents of which is incorporated by reference herein.

BACKGROUND

Techniques exist to control a computer system via a wireless myoelectric user interface. In one such approach, a user wears a band that is sized to fit around the user's forearm or wrist. The band includes myoelectric sensors arranged to detect hand and/or finger gestures by sensing the user's muscle activity. Typically, the wearable band includes processing capabilities to receive the sensed signals and to convert them into electronic control signals, which are then delivered (wirelessly or otherwise) to a device being controlled, such as computer, some other portable electronic device, an application executing on such a device, or the like.

Additionally, research studies investigating a brain-computer interface (BCI), also known as a brain-machine interface (BMI), a mind-machine interface (MMI) or a direct neural interface (DNI), have shown that a direct communication pathway is established between an enhanced or wired brain, and an external device. BCIs are often directed at researching, mapping, assisting, augmenting, or repairing human cognitive or sensory-motor functions.

SUMMARY

Some conventional brain control interfaces use signals directly recorded from cortical neurons in the brain to provide adaptive control of a device. Some embodiments are directed to providing enhanced adaptive control of a device without the use of a cortical interface. Rather, some embodiments are directed to a system for recording a continuous time series of neuromuscular signals using neuromuscular sensors. The neuromuscular signals are provided as the front-end to an adaptive control system to control a device. The neuromuscular signals may also be used in combination with information about how users typically control the device to train a statistical model for associating neuromuscular signals with intended control actions.

Controlling a device such as a game controller for a computer game typically requires a user to learn how interacting with different controls on the device results in a desired action in the computer game. How the user may interact with the device to perform a desired action is restricted based on how the device was programmed to translate user interactions with the device into control signals. For example, a joystick game controller for controlling the direction that a computer-generated image in a computer game moves on a display may be programmed to generate a first control signal when the user pushes the joystick to the right and a second control signal when the user pushes the joystick to the left. The corresponding control signals generated by the control device are provided to the computer to control the direction that the computer-generated image moves. The inventors have recognized and appreciated that existing control systems that require a user to learn the operation of the device are inflexible and generally cannot be tailored to how a user prefers to interact with the device. Some embodiments are directed to a technique for training a control system to translate user-specific body movements into control signals for controlling a device. Such embodiments provide for a highly-configurable control interface that enables different users to control devices according to their preferences and without restrictions placed on the control device by the device manufacturer.

Some embodiments are directed to an adaptive system for deriving control signals from measurements of muscle or motor unit activity. The system adapts a statistical model of user intention based on measurements of neuromuscular activity as the user controls a (e.g., a computer application or other effector). In some embodiments, the control signals are computed by a control mapping in real-time or substantially real-time as neuromuscular activity data is received from the plurality of sensors.

In some embodiments, a computer is programmed to execute one or more signal processing algorithms that map a time series of sensor signals to control signals that the computer provides as inputs to an effector (e.g., a user interface program). An intention model that models a user's intentions based on task-specific information is dynamically updated at the user performs the task to improve the control mapping from the sensor signals to the control signal. In some embodiments, the control mapping is adapted based on collected data by performing a regression or classification analysis with estimates of intended signals to map sensor signals to continuous or discrete inputs, respectively. In some embodiments, the resulting adaptive control mapping provides increased fidelity of control, reduced user effort required for equivalent control, and allow for adaptation to changes in a user's signaling behavior.

An adaptive control technique in accordance with some embodiments uses EMG or other neuromuscular signals as the source signal for control with adaptive feedback. The approach obviates invasive approaches that require direct neural interaction with cortical neurons. The relevant neural signals used for the adaptive control are synthetically constructed using the neuromuscular data, which provides for less costly and invasive processing. Further, the adaptive control approach described herein in accordance with some embodiments may be carried out in real-time due to the ease in switching between the recorded neuromuscular data and the synthesized neural data streams. The approach alters a conventional BCI paradigm by capturing signals used to force muscle contraction (e.g., EMG signals), and redirects those signals for an arbitrary adaptive control. The estimated control signal generated in accordance with some embodiments can be used to control any application or device that requires or otherwise benefits from continuous control.

Some embodiments are directed to techniques for controlling applications including, but not limited to, virtual reality, augmented reality, and mobile computing technology.

According to one aspect, a system for adapting a control mapping associating sensor signals with control signals for controlling an operation of a device is provided. The system comprises a plurality of sensors including a plurality of neuromuscular sensors arranged on one or more wearable devices, wherein the plurality of neuromuscular sensors are configured to continuously record neuromuscular signals from a user. The system further comprises at least one computer hardware processor and at least one non-transitory computer-readable storage medium storing processor-executable instructions that, when executed by the at least one computer hardware processor, cause the at least one computer hardware processor to perform: obtaining first state information for an operation of the device; providing the first state information as input to an intention model associated with the operation of the device and obtaining corresponding first intention model output; providing the neuromuscular signals and/or signals derived from the neuromuscular signals as inputs to a first control mapping and obtaining corresponding first control mapping output; and updating the first control mapping using the inputs to the first control mapping and the first intention model output to obtain a second control mapping.

According to another aspect, a method of adapting a control mapping associating sensor signals with control signals for controlling an operation of a device is provided. The method comprises obtaining a plurality of sensor signals from a plurality of sensors including a plurality of neuromuscular sensors arranged on one or more wearable devices, wherein the plurality of neuromuscular sensors are configured to continuously record neuromuscular signals from a user; obtaining first state information for an operation of a device; providing the first state information as input to an intention model associated with the operation of the device and obtaining corresponding first intention model output; providing the neuromuscular signals and/or signals derived from the neuromuscular signals as inputs to a first control mapping and obtaining corresponding first control mapping output; and updating the first control mapping using the inputs provided to the first control mapping and the first intention model output to obtain a second control mapping.

According to another aspect, a non-transitory computer-readable storage medium encoded with a plurality of instructions that, when executed by at least one computer hardware processor perform a method is provided. The method comprises: obtaining a plurality of sensor signals from a plurality of sensors including a plurality of neuromuscular sensors arranged on one or more wearable devices, wherein the plurality of neuromuscular sensors are configured to continuously record neuromuscular signals from a user; obtaining first state information for an operation of a device; providing the first state information as input to an intention model associated with the operation of the device and obtaining corresponding first intention model output; providing the neuromuscular signals and/or signals derived from the neuromuscular signals as inputs to a first control mapping and obtaining corresponding first control mapping output; and updating the first control mapping using the inputs provided to the first control mapping and the first intention model output to obtain a second control mapping.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

DETAILED DESCRIPTION

Some conventional brain machine interfaces record brain (e.g., cortical) signals and map the recorded brain signals to corresponding control signals for controlling a prosthetic limb resulting in an executed movement of the prosthetic device. Although such brain machine interface techniques are useful to enable patients to self-control prosthetic devices using a patient's own brain signals, implementing such techniques is quite invasive, as they require direct access to the cortical neurons in the brain to record the biological signals that are used to provide the control signals. The inventors have recognized and appreciated that conventional control interfaces may be improved by measuring biophysical signals corresponding to a user's movements using a plurality of sensors (e.g., EMG sensors) worn by a user, and mapping the movement information recorded by the sensors to control signals used to control a device.

Figure 1:
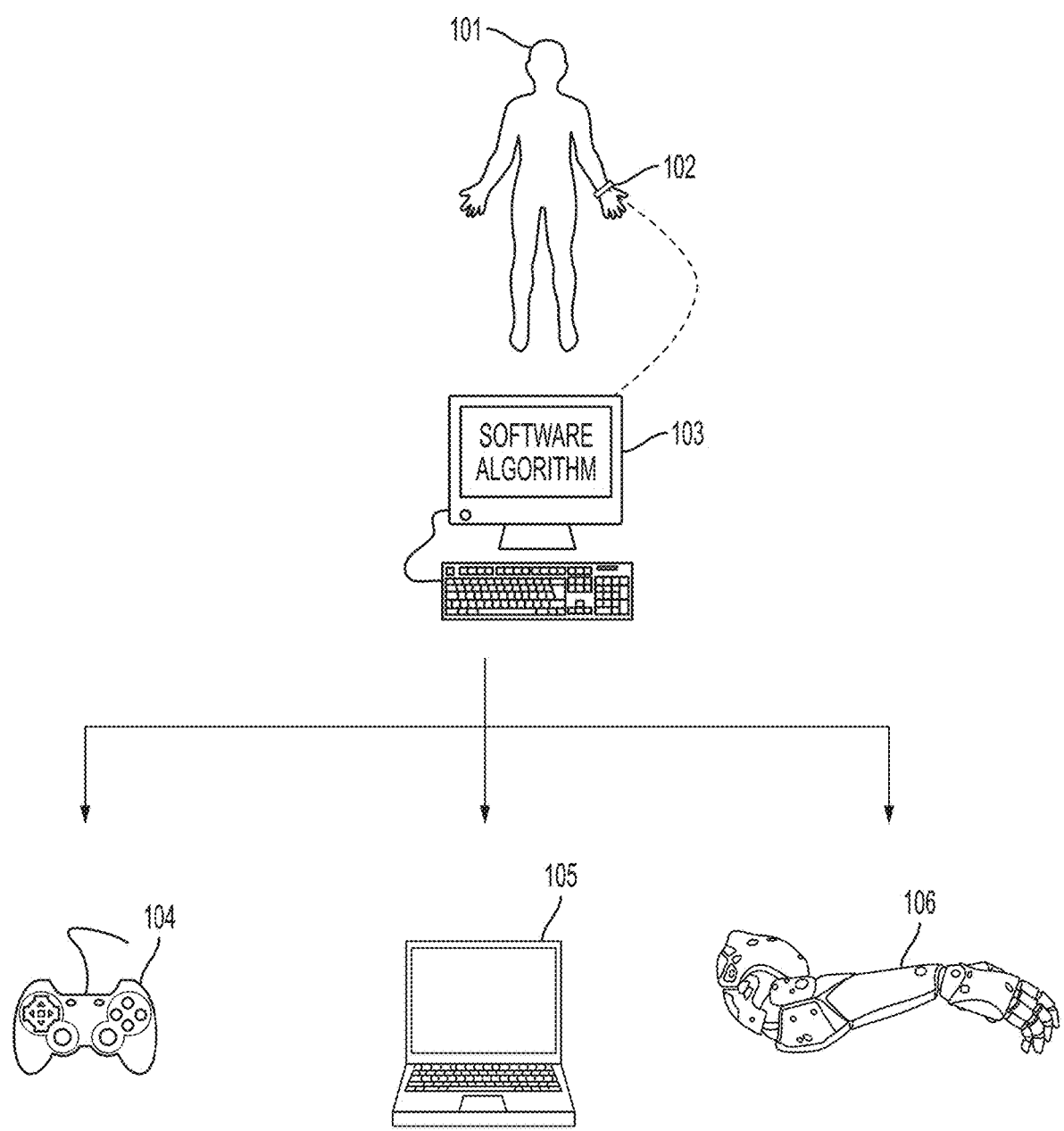
FIG. 1 depicts a control process in accordance with some embodiments of the technology described herein.

FIG. 1 illustrates components of a system for mapping signals recorded from sensors 102 worn by user 101 to control signals that are subsequently provided to a user-interactive program (or, more generally, a user interface) in accordance with some embodiments. Sensors 102 are configured to record signals resulting from the movement of portions of a human body. Sensors 102 may include one or more Inertial Measurement Units (IMUs), which measure a combination of physical aspects of motion, using, for example, an accelerometer and a gyroscope. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso (e.g., arms, legs) as the user moves over time.

Sensors 102 may also include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) describing the movement (e.g., for portions of the user's body distal to the user's torso, such as hands and feet) may be predicted based on the sensed neuromuscular signals as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso, whereas the neuromuscular sensors may be arranged to detect movements of one or more body segments distal to the torso. It should be appreciated, however, that sensors 102 may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, a plurality of EMG sensors are arranged on a wearable device configured to be worn around the lower arm or wrist of a user. In such an arrangement, the EMG sensors may be configured to determine movement information associated with wrist or hand segments to determine, for example, whether the user has an open or closed hand configuration.

Each of sensors 102 include one or more movement sensing components configured to sense movement information. In the case of IMUs, the movement sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the movement sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the movement sensing components may be processed using hardware signal processing circuitry (e.g., to perform amplification, filtering, and/or rectification). In other embodiments, at least some signal processing of the output of the movement sensing components may be performed in software. Thus, signal processing of autonomous signals recorded by sensors 102 may be performed in hardware, software, or by any suitable combination of hardware and software, as aspects of the technology described herein are not limited in this respect.

In some embodiments, the recorded sensor data may be processed to compute additional derived measurements that are then used to control a device, as described in more detail below. For example, recorded signals from an IMU sensor may be processed to derive spatial information (e.g., orientation, position, estimated joint angle) that specifies the spatial position of a rigid body segment over time. Sensors 102 may implement signal processing using components integrated with the movement sensing components, or at least a portion of the signal processing may be performed by one or more components in communication with, but not directly integrated with the movement sensing components of the sensors.

In some embodiments, at least some of the plurality of sensors 102 are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the sensors may be arranged on a wearable patch configured to be affixed to a portion of the user's body.

Figure 6:
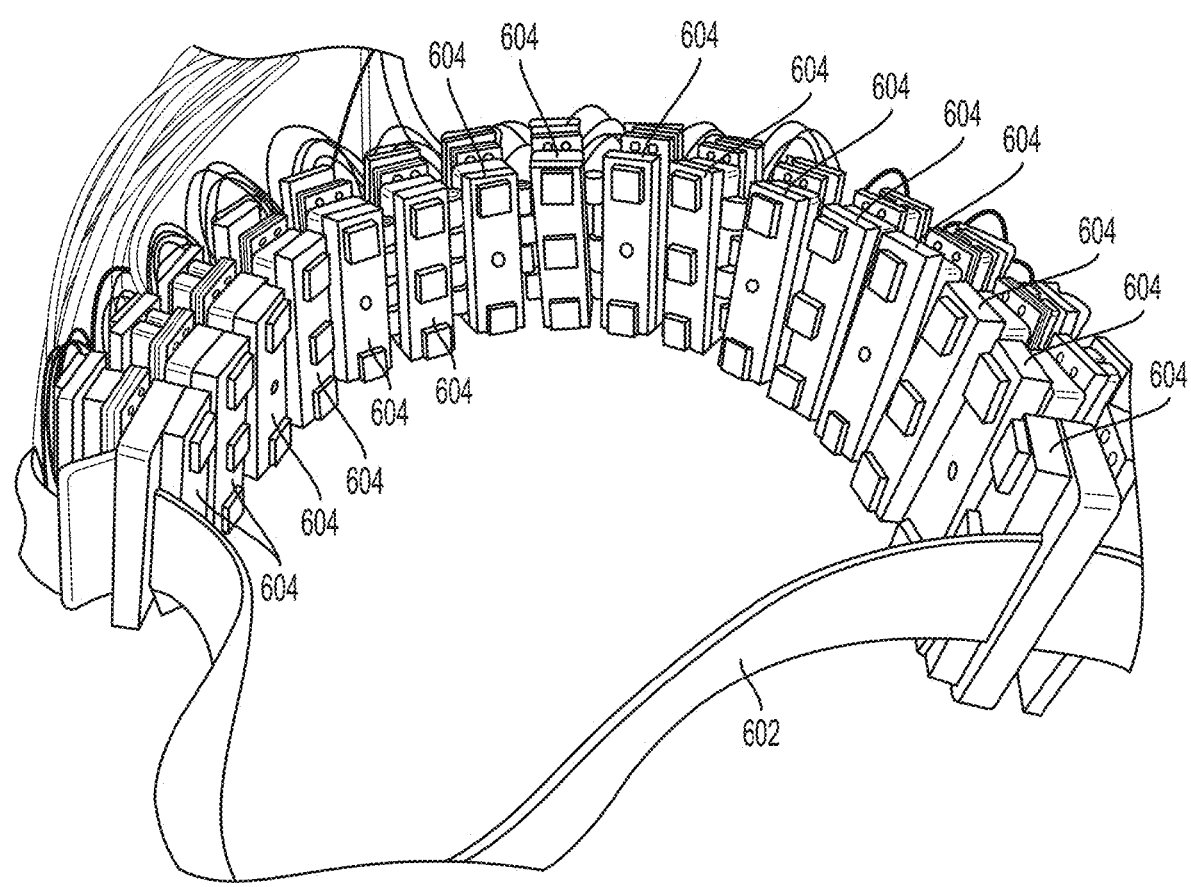
FIG. 6 illustrates a wristband having EMG sensors arranged circumferentially thereon, in accordance with some embodiments of the technology described herein.
Figure 7:
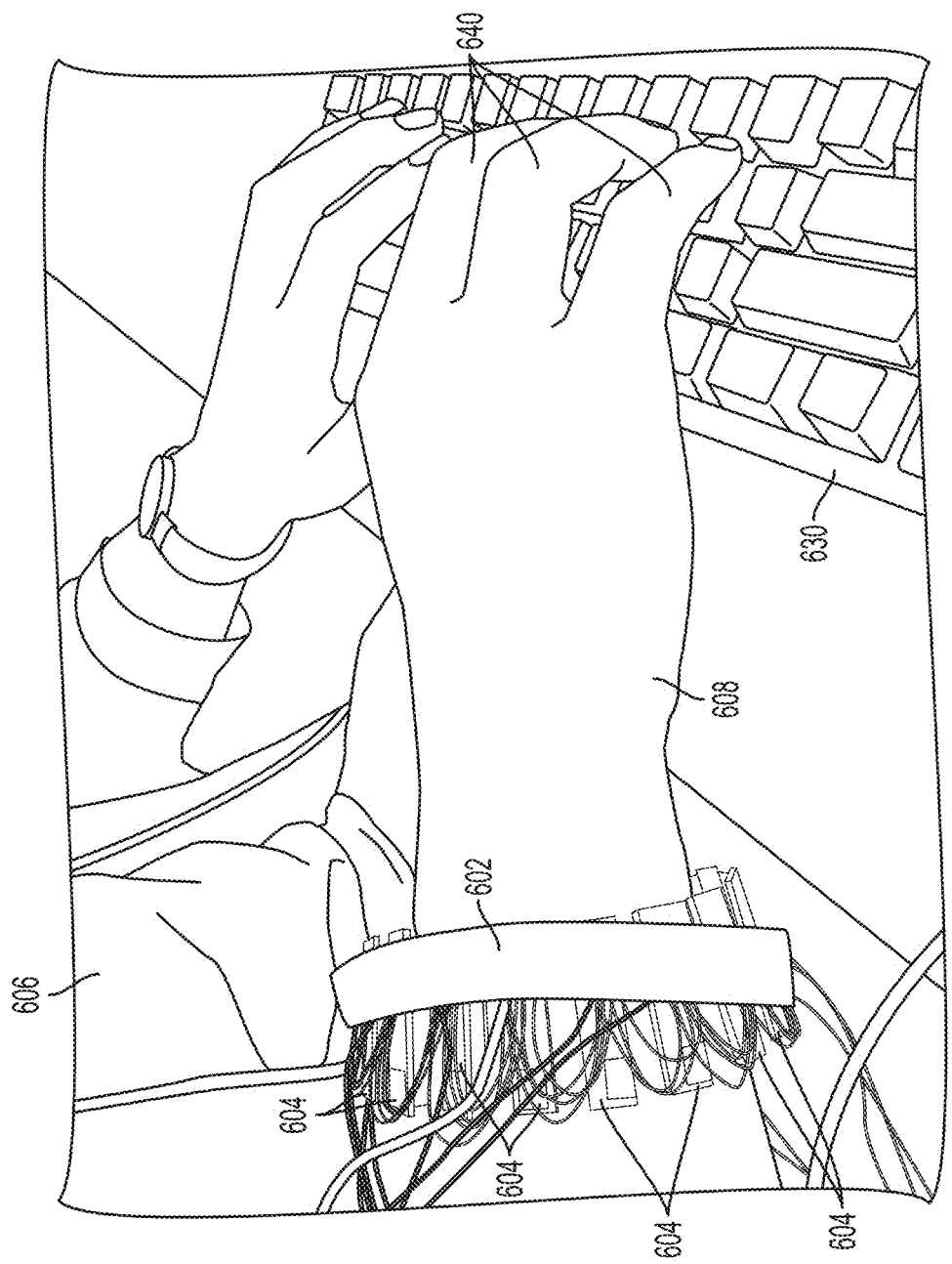
FIG. 7 illustrates a user wearing the wristband of FIG. 6 while typing on a keyboard, in accordance with some embodiments of the technology described herein.

In one implementation, 16 EMG sensors are arranged circumferentially around an elastic band configured to be worn around a user's lower arm. For example, FIG. 6 shows EMG sensors 604 arranged circumferentially around elastic band 602. It should be appreciated that any suitable number of neuromuscular sensors may be used and the number and arrangement of neuromuscular sensors used may depend on the particular application for which the wearable device is used. For example, a wearable armband or wristband may be used to generate control signals for controlling throwing a ball by an avatar in a computer-generated virtual reality environment, whereas a wearable leg or ankle band may be used to generate control signals for controlling kicking a ball by the avatar. For example, as shown in FIG. 7, a user 606 may be wearing elastic band 602 on hand 608. In this way, EMG sensors 604 may be configured to record EMG signals as a user controls keyboard 630 using fingers 640. In some embodiments, elastic band 602 may also include one or more IMUs (not shown), configured to record movement information, as discussed above.

In some embodiments, multiple wearable devices, each having one or more IMUs and/or neuromuscular sensors included thereon may be used to control a device.

The system also includes one or more computer processors 103 programmed to communicate with sensors 102. For example, signals recorded by one or more of the sensors 102 may be provided to processor(s) 103, which may be programmed to perform signal processing, non-limiting examples of which are described above. Although illustrated as software in FIG. 1, processor(s) 103 may be implemented in hardware, firmware, software, or any combination thereof. Additionally, processor(s) 103 may be co-located on a same wearable device as one or more of the sensors or may be at least partially located remotely (e.g., processing may occur on one or more network-connected processors).

The system also includes one or more non-transitory computer-readable storage devices in communication with processor(s) 103. The storage devices may be configured to store information describing one or more statistical models (e.g., an intention model), examples of which are described in more detail below.

In some embodiments, processor(s) 103 may be configured to communicate with one or more of sensors 102, for example to calibrate the sensors prior to measurement of movement information. For example, a wearable device may be positioned in different orientations on or around a part of a user's body and calibration may be performed to determine the orientation of the wearable device and/or to perform any other suitable calibration tasks. Calibration of sensors 102 may be performed in any suitable way, and embodiments are not limited in this respect. For example, in some embodiments, a user may be instructed to perform a particular sequence of movements and the recorded movement information may be matched to a template by virtually rotating and/or scaling the signals detected by the sensors (e.g., by the electrodes on EMG sensors). In some embodiments, calibration may involve changing the gain(s) of one or more analog to digital converters (ADCs), for example, in the case that the signals detected by the sensors result in saturation of the ADCs.

The system of FIG. 1 also includes one or more controllers configured receive a control signal based, at least in part, on processing by processor(s) 103. As shown, non-limiting examples of controller include, but are not limited to, a game controller 104, a computer 105 and a prosthetic device 106. As discussed in more detail below, processor(s) 103 may implement one or more trained statistical models configured to generate control signals determined based, at least in part, on signals recorded by sensors 102 worn by a user. One or more control signals determined based on the output of the trained statistical model(s) may be sent to the one or more controllers to control one or more operations of a device associated with the controller. In some embodiments, the controller(s) include a display controller configured to instruct a visual display to display a graphical representation (e.g., a bar on the screen, a graphical representation of the user's body or a graphical representation of a character (e.g., an avatar in a virtual reality environment)) based on the provided control signals. In other embodiments, the controller(s) include a controller of a physical device, such as a robot or prosthetic device. Control signals sent to the controller may be interpreted by the controller to operate one or more components of the robot to move in a manner that corresponds to the movements of the user as sensed using the sensors 102.

Any suitable controller, configured to control one or more physical or virtual devices, may be used in accordance with embodiments of the technology described herein. Non-limiting examples of physical devices that may be controlled include consumer electronics devices (e.g., television, smartphone, computer, laptop, telephone, video camera, photo camera, video game system, appliance, etc.), vehicles (e.g., car, marine vessel, manned aircraft, unmanned aircraft, farm machinery, etc.), robots, weapons, or any other device that may receive control signals from processor(s) 103.

Non-limiting examples of applications of some embodiments of the techniques described herein include menu navigation, buttons, dials, levers, selection of items, typing without a physical keyboard or keypad in either a desktop or mobile setting, cut/paste operations for document editing, cursor control, scrolling and volume control. Non-limiting examples of applications further include mechanisms for controlling non-visual user interfaces, such as auditory or tactile menus or games. Non-limiting examples of applications also include systems for controlling a prosthetic limb, systems for facilitating gestural communication between people, and manipulation of higher dimensional data, such as three-dimensional and rotational data. Non-limiting examples of applications still further include wake and unlock gestures for phones and computers, biometric codes and keys, and home appliance controls.

As a user interacts with the user-interactive program or other controlled device, sensor data is collected by sensors. The collected sensor data and the user's interaction with the device enables the system to learn how to modify the mapping between the recorded sensor signal and control signals sent to the controllers. In this way, the signals recorded by the wearable sensors is used to both control a device and facilitate learning by the control system to map the user's body movements to intended actions.

Figure 2:
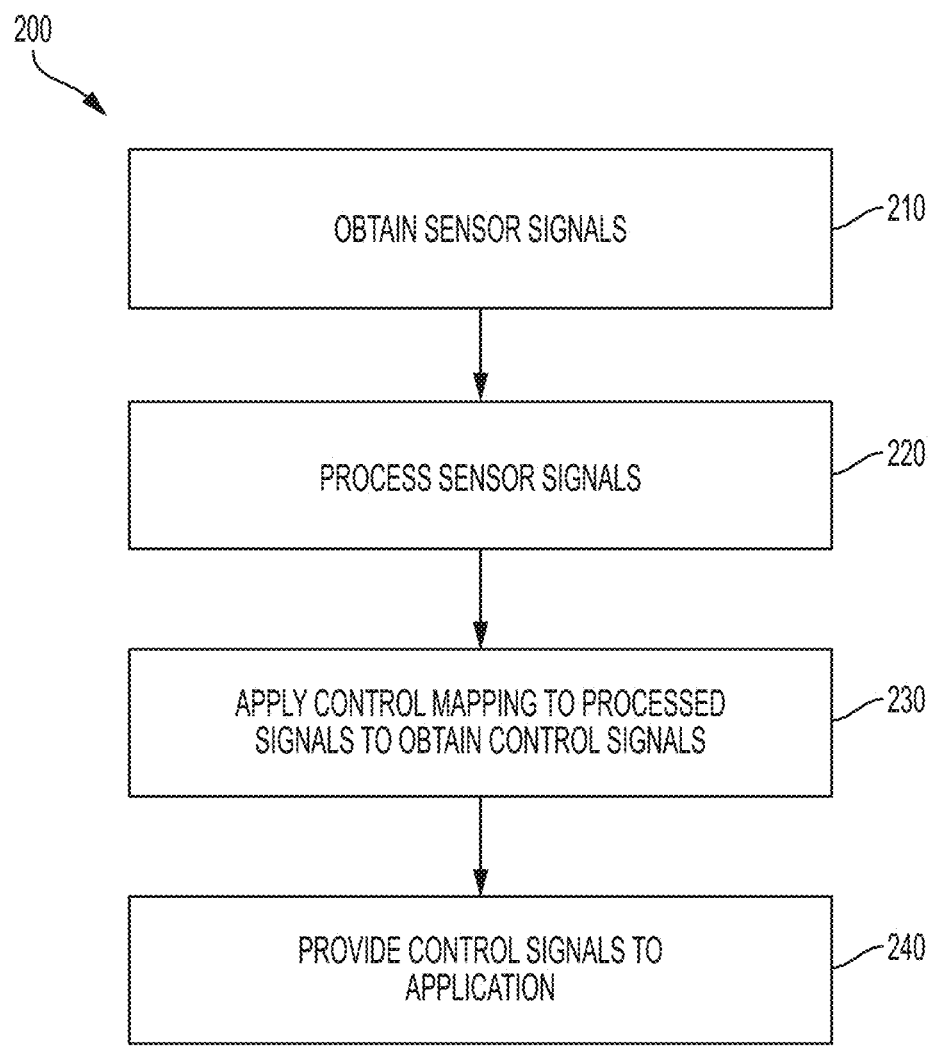
FIG. 2 illustrates a process for controlling a device in accordance with some embodiments of the technology described herein.

FIG. 2 describes a process 200 for providing control signals to a control device (e.g., a controller of a computer application) based on neuromuscular signals (e.g., EMG signals, MMG signals, SMG signals). The terms "effector" and "control device" are used interchangeably herein, and both terms refer to an entity that is being controlled by the control signals output from a control mapping, as discussed in more detail below. Although process 200 is described herein with respect to EMG signals, it should be appreciated that process 200 may be used to provide control signals based on EMG signals, MMG signals, SMG signals, or any suitable combination thereof, or based on neuromuscular signals in combination with additional sensor signals (e.g. data from inertial measurement units).

Process 200 may be executed by any suitable computing device(s), as aspects of the technology described herein are not limited in this respect. For example, process 200 may be executed by processors 103 described with reference to FIG. 1. As another example, one or more acts of process 200 may be executed using one or more servers (e.g., servers part of a cloud computing environment). Process 200 begins at act 210, where a plurality of autonomous signals are obtained from a plurality of sensors (e.g., EMG sensors) worn by a user.

In some embodiments, the signals obtained at act 210 are pre-processed in act 220 using amplification, filtering, rectification or other types of signal processing. In some embodiments, the filtering may comprise temporal filtering implemented using convolution operations and/or equivalent operations in the frequency domain (e.g., after the application of a discrete Fourier transform). In some embodiments, the pre-processing may comprise dimensionality reduction (e.g. non-negative matrix factorization (NMF), principal component analysis (PCA), independent component analysis (ICA)), estimation of derived muscle activity signals, spike sorting, spectral decomposition, estimation of derived features (e.g., joint angles) and/or other forms of feature extraction. The result of this preprocessing is set of derived signals from which to compute control signals.

The inventors have appreciated that using EMG signals recorded from a user obviates the cortical interface required in some conventional machine control interfaces in effect by re-purposing the EMG data for adaptive control, in particular by generating a set of derived signaling that synthesizes neural data streams from the recorded EMG data. In some embodiments, the neuromuscular signals that are otherwise used by the body to move one or more muscles or muscle groups are collected (e.g., using a wearable sensor array) and re-purposed for arbitrary adaptive control of a device (e.g., a computer programmed to present a user interactive application).

Next, process 200 proceeds to act 230, where a control mapping is applied to the processed sensor signals to map the sensor signals to control signals. In some embodiments, the control mapping maps a time series of one or more processed sensor signals to one or more control signals. In some embodiments, this mapping acts on sensor signal data from a single time point to produce corresponding sensor control signals for that time point. In some embodiments, the output of the control mapping may depend on input signals from multiple time points, non-limiting examples of which include stateful mappings (e.g., a Kalman filter or recurrent network) and mappings acting on inputs at multiple time lags (e.g. temporal convolutions).

In some embodiments, the control mapping is a linear mapping represented by a matrix with number of rows equal to the number of control signals and number of columns equal to the number of processed sensor signals, such that the control signals are computed by multiplying the processed sensor signals processed in act 220 by this matrix. It should be appreciated, however, that the control mapping is not limited to being a linear mapping and may be of any other suitable form. For example, in some embodiments the control mapping may be a generalized linear model, neural network, recurrent neural network, convolutional network, finite state machine, Kalman filter, dynamical system, hidden Markov model, Markov switching model, dynamic Bayesian network, and/or any other suitable computational mapping.

Next, process 200 proceeds to act 240, where the computed control signals are transmitted to an effector. Non-limiting examples of effectors include a computer game, computer program, prosthetic limb, robot, or vehicle. Non-limiting examples of tasks include a playing a computer game, entering text into a computer application, moving a cursor to a desired location, picking up an object with a prosthetic arm, or driving a vehicle.

Figure 3:
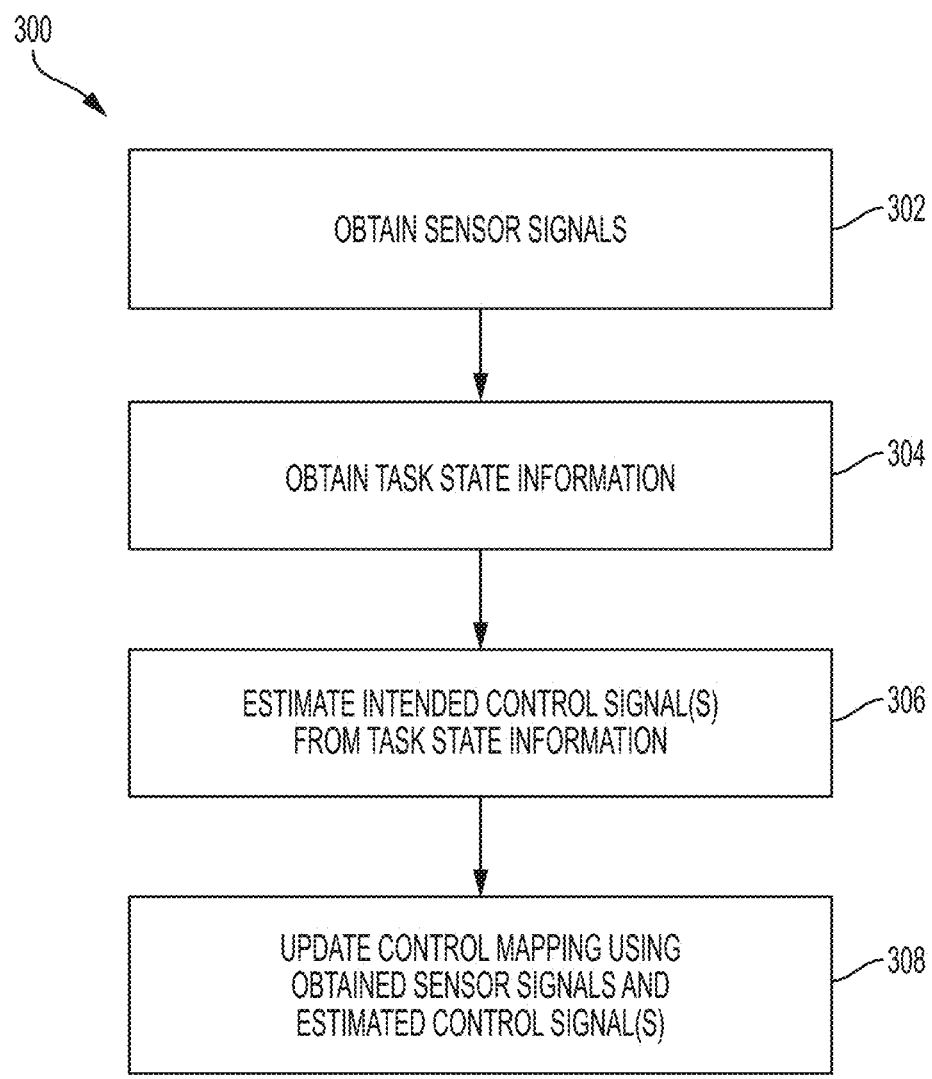
FIG. 3 illustrates a process for updating a control mapping using autonomous sensor signals in accordance with some embodiments of the technology described herein.

FIG. 3 illustrates a process 300 for adapting a control mapping in accordance with some embodiments. Although process 300 is described herein with respect to EMG signals, it should be appreciated that process 300 may be used to adapt a control mapping taking as input any recorded neuromuscular signals including, but not limited to, EMG signals, MMG signals, SMG signals, or any combination of EMG signals, MMG signals, and SMG signals. Additionally, in some embodiments, other signals (e.g., signals recorded by IMUs, signals derived from IMU measurements) may be used to adapt the control mapping.

Process 300 begins in act 302, where signals recorded by a plurality of sensors are obtained. Examples of obtaining sensor signals are described above in connection with the process of FIG. 2. The process 300 then proceeds to act 304, where the system obtains data containing information about the state of a task with which a user is engaged by using the effector to which control signals are transmitted in act 240. In some embodiments, the state of the task is determined in combination with other control signals. The information about the state of the task (also referred to herein as "task information") may be determined in any suitable way. In some embodiments, additional sensors may be used for obtaining task information. For example, in the illustrative case of a user manipulating an object with a prosthetic limb, cameras and/or position sensors may be used to obtain task information such as the relative positions of the prosthetic limb and the object being manipulated. In some embodiments, for example in the case of a computer-based task, information about the state of the task may be obtained using an application programming interface (API) and/or screen capture. In some embodiments, data containing information about the state of the task undergoes processing (e.g. image segmentation and or other image processing).

Process 300 next proceeds to act 306, where one or more control signals are estimated based on the obtained sensor signals and the obtained task information describing a state of the task. Some embodiments are configured to implement a statistical intention model that predicts the user's intended control signals. Inputs to the intention model include, but are not limited to, information about the state of the task obtained by the system in act 304. In some embodiments, the acquired neuromuscular signals, the control mapping, the control signals output from the control mapping, or any combination thereof may also be provided as input to the intention model.

In some embodiments, the intention model is a task-specific model of user behavior. The task-specific model may be implemented as a statistical model constructed based on heuristic or intuitive approximation of user behavior within the context of the task. A non-limiting illustrative example of such an intention model is provided in the case that the task is the computer game Pong, in which the user controls the one-dimensional velocity of a paddle to intercept the trajectory of a ball. In this example, the intention model takes as input the position of the user-control paddle and the position and velocity of the ball and provides as output an estimate of the velocity control signal that the user intends to provide to the paddle. According to one non-limiting intention model, the intended paddle velocity is proportional to the distance from the paddle's current position to the target position to which the paddle must be moved to intercept the trajectory of the ball, e.g., intended_velocity=proportionality_constant*(target_position−position_paddle).

In some embodiments, the intention model may be configured to continuously provide estimates of the user's intended control signals, whereas in other embodiments, the intention model may be configured to provide estimates only at specific times. For example, in the illustrative example of Pong, the intention model would, in some embodiments, output estimates for the user's intended control signals only at times at which the ball moves toward the line along which the user's paddle could move, and not providing estimates at times during which the ball moves away from this line.

In some embodiments, the intention model is configured to compute its estimate of the user's intention at each time point based on inputs corresponding to times no later than that of the user's estimated intention. The aforementioned illustrative example of an intention model for the computer game Pong provides an example of such an embodiment in which the user's intention at a given time is estimated based upon the state of the task at that same time. In this example, the intention model is configured to estimate the user's intended control signals substantively in real time.

In some other embodiments, the intention model computes estimates of the user's intention based upon inputs corresponding to times that include, but are not limited to, times later than the time for which the user's intention is being estimated. A non-limiting illustrative example of an intention model using inputs corresponding to later times to estimate the user's intended control signals at an earlier time is provided herein within the context of a task in which a user controls a cursor to navigate to and click on an icon from a selection of possible choices presented on a computer screen. According to some non-limiting implementations of an intention model for such as task, the intention model may not output estimates of the user's intended cursor velocity until the user clicks on one of the icons. Following the user's selection of the icon, the intention model is configured to estimate the user's intended cursor velocity control signal at an earlier time to be in the direction of a vector pointing from the cursor position at the time for which the intention is being estimated to the cursor position at the time when the user clicked on the icon.

In some embodiments, the intention model is a trained statistical model. In some embodiments, the outputs of the intention model are point estimates (e.g. maximum likelihood estimates) of the user's intended control signals. In some embodiments, the outputs of the intention model are probability distributions over possible values of the user's intended control signals. For example, the intention model may output probabilities of discrete control signals or parameters for distributions (e.g. mean and variance of the Gaussian distribution) over continuously valued control signals.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

It should be appreciated that aspects of the technology described herein are not limited to using neural networks, as other types of statistical models may be employed in some embodiments. For example, in some embodiments, the statistical model may comprise a generalized linear model, a hidden Markov model, a Markov switching model, dynamic Bayesian networks, and/or any other suitable graphical model having a temporal component.

In some embodiments, values for parameters of the statistical model may be estimated from the training data generated as one or more users perform one or more tasks. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a mean-squared error loss function (e.g. in the case of continuous control signals), a cross-entropy loss function (e.g. in the case of discrete control signals) and/or any other suitable loss function, as aspects of the technology described herein are not limited in this respect.

In some embodiments, the statistical model may be trained with training data generated as one or more users performs one or more tasks. The training data may include data generated as one or more users performs one or more tasks using, at least in part, the control process 200, using one or more control systems independent of process 200 (e.g. controlling a computer game using a keyboard and/or mouse), as the invention is not limited by the method for generating and parameterizing the intention model.

In some embodiments, the intention model may be parameterized without the use of training data. As a non-limiting example, some embodiments may include an intention model based upon a control policy with parameters computed using dynamic programming or learned through reinforcement learning. In some embodiments, training data for the intention model may combine data generated as one or more human users performs one or more tasks with data generated computationally from a task simulation with a computational control policy.

In some embodiments, one or more of the user's intended control signals, the recorded neuromuscular signals, information derived from the neuromuscular signals (e.g., orientation, estimated joint angles), the processed (e.g., filtered, amplified, rectified) neuromuscular signals, information associated with sufficient statistics for characterizing the neuromuscular signals, inputs to and/or outputs from the intention model, and inputs to and/or outputs from the control mapping may be stored on one or more non-transitory computer readable mediums in communication with processor(s) 103.

Process 300 next proceeds to act 308, where estimates of the user's intended control signals and processed neuromuscular signals are aggregated to produce training data for adapting the control mapping. The obtained data may be combined and further processed in any suitable way. In some embodiments, at least some of the data may be resampled (e.g., up-sampled or down-sampled) such that all training data corresponds to time series data at the same time resolution. Resampling at least some of the data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

The control mapping is then updated using the training data. Updating of the control mapping may occur substantively in real time as a user performs the task in accordance with process 200, may occur intermittently as the user performs the task, may occur off-line between uses of process 200 to control the task, and/or may occur according to any suitable schedule or combination of schedules as the invention is not limited with respect to the timing and frequency at which the control mapping is updated. The updated control mapping is then used it act 230 of process 200.

Figure 5:
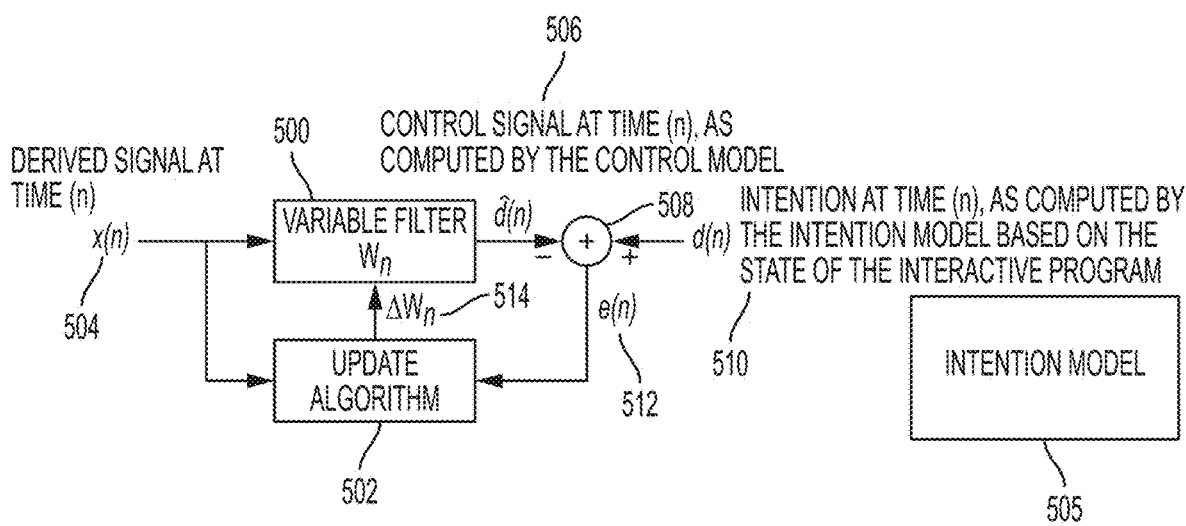
FIG. 5 is a diagram illustrating control mapping adaptation in accordance with some embodiments of the technology described herein.

FIG. 5 depicts a method in accordance with some embodiments, in which the control mapping between recorded autonomous signals and control signals is a linear filter that is updated using the recursive least squares (RLS) algorithm. The terms "control mapping" and "control model" are used herein interchangeably, and both mean the mapping from sensor signals to control signals that is adapted using one or more of the techniques described herein. As depicted, the parameters of the control model may be implemented as variable filter coefficients 500, and the update algorithm 502 may comprise an RLS algorithm, examples of which are known in the art. The derived (e.g., preprocessed) signal at time (n) 504 is provided to variable filter 500, which outputs a control signal $\hat{d}(n)$ at time (n) 506, as computed by the control model. Element 508 receives control signal $\hat{d}(n)$, together with the estimated intention e(n) at time (n) 510, as predicted by the intention model 505 based on the state of the task, as described above. The update algorithm 502 uses the derived signal 504 and an error 512 between signals 506 and 508 to compute an update 514 to the parameters of the control model (i.e., an update to the control mapping).

It should be appreciated that aspects of the technology described herein are not limited to using an RLS algorithm, as other types of learning and/or optimization algorithms may additionally or alternatively be employed. For example, in some embodiments, the control mapping may be updated using expectation maximization, gradient descent, stochastic gradient descent, and/or any other suitable iterative optimization technique. In embodiments where the control mapping is implemented as a recurrent neural network (e.g., an LSTM), the statistical model may be updated using stochastic gradient descent and backpropagation through time. The updating algorithm may employ a mean-squared error loss function (e.g. in the case of continuous control signals), a cross-entropy loss function (e.g. in the case of discrete control signals) and/or any other suitable loss function, as aspects of the technology described herein are not limited in this respect.

In some embodiments, a control mapping adapted in the context of one task may be used for control of one or more additional tasks. As an illustrative example, a control mapping may first be adapted in the context of a task in which the user controls a cursor to select an icon on a computer screen. Later, the same control mapping may be used to control an operation of a physical or virtual vehicle, for example by mapping the control signal for the vertical movement of the cursor to the acceleration and/or braking of the vehicle and the control signal for the horizontal movement of the cursor to the steering of the vehicle. The control mapping may or may not continue to be adapted in the context of the additional tasks, as aspects of some embodiments are not limited in this respect.

Figure 4:
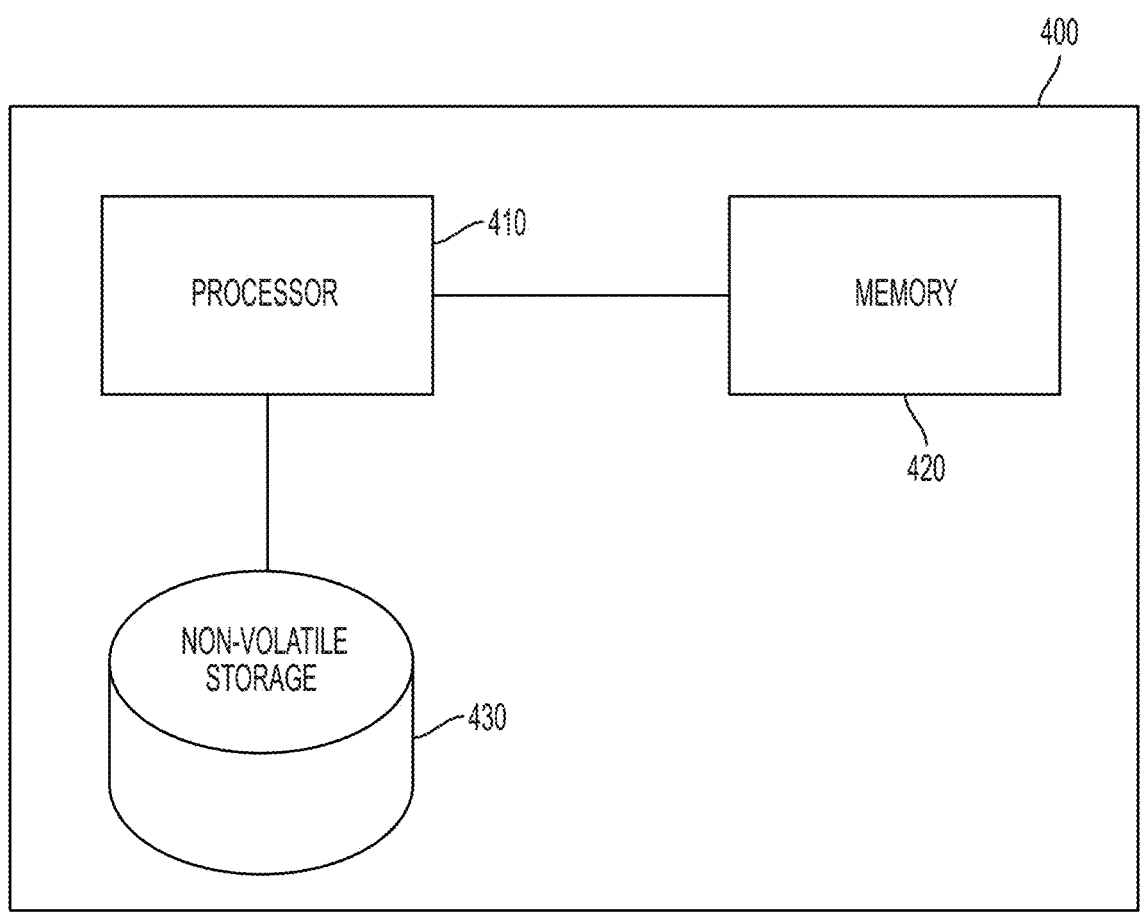
FIG. 4 is a diagram of an illustrative computer system that may be used in implementing some embodiments of the technology described herein.

An illustrative implementation of a computer system 400 that may be used in connection with any of the embodiments of the disclosure provided herein is shown in FIG. 4. The computer system 400 may include one or more processors 410 and one or more articles of manufacture that comprise non-transitory computer-readable storage media (e.g., memory 420 and one or more non-volatile storage media 430). The processor 410 may control writing data to and reading data from the memory 420 and the non-volatile storage device 430 in any suitable manner. To perform any of the functionality described herein, the processor 410 may execute one or more processor-executable instructions stored in one or more non-transitory computer-readable storage media (e.g., the memory 420), which may serve as non-transitory computer-readable storage media storing processor-executable instructions for execution by the processor 410.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples (e.g., the processes described with reference to FIGS. 2 and 3) have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system for adapting a control mapping associating sensor signals with control signals for controlling an operation of a device, the system comprising:
    a plurality of sensors including a plurality of neuromuscular sensors arranged on one or more wearable components, wherein the plurality of neuromuscular sensors are configured to continuously record neuromuscular signals from a user;
    at least one computer hardware processor;
    at least one non-transitory computer-readable storage medium storing processor-executable instructions that, when executed by the at least one computer hardware processor, cause the at least one computer hardware processor to perform:
    obtaining first state information for an operation of the device, wherein the first state information includes information relating to the state of a task;
    providing the first state information as input to an intention model associated with the operation of the device and obtaining a first intention model output including an estimate of an intended control signal;
    providing the neuromuscular signals and/or signals derived from the neuromuscular signals as inputs to a first control mapping and obtaining a first control mapping output;
    comparing the first control mapping output with the estimate of the intended control signal;
    updating the first control mapping using the inputs to the first control mapping and the first intention model output to obtain a second control mapping, and
    controlling the device using a control signal based on the second control mapping.

2. The system of claim 1, wherein the processor-executable instructions that, when executed by the at least one computer hardware processor, cause the at least one computer hardware processor to perform:
    obtaining a new set of neuromuscular signals from the plurality of neuromuscular sensors;
    providing the new set of neuromuscular signals and/or signals derived from the new set of neuromuscular signals as inputs to the second control mapping to obtain a second control mapping output;
    comparing the the second control mapping output with a second estimate of the intended control signal, and determining a third control mapping; and
    controlling the device using the third control mapping.

3. The system of claim 1, wherein the processor-executable instructions that, when executed by the at least one computer hardware processor, cause the at least one computer hardware processor to perform:
    obtaining second state information for an at least one user-interactive application;
    providing the second state information as input to the intention model associated with the operation of the device and obtaining a second intention model output; and
    updating the second control mapping using the inputs provided to the second control mapping and the second intention model output to obtain a third control mapping.

4. The system of claim 1, wherein updating the first control mapping using the inputs provided to the first control mapping and the first intention model output to obtain the second control mapping is performed using a recursive least squares (RLS) technique.

5. The system of claim 4, wherein the RLS technique is configured to fit a linear model that predicts velocity control signals indicating the user's control intentions from the neuromuscular signals.

6. The system of claim 1, wherein the intention model is a trained statistical model implemented as a recurrent neural network.

7. The system of claim 6, wherein the recurrent neural network is a long short-term memory (LSTM) neural network.

8. The system of claim 1, wherein the intention model is trained statistical model implemented as a non-linear regression model.

9. The system of claim 1, wherein the neuromuscular sensors comprise electromyography (EMG) sensors, mechanomyography (MMG) sensors, sonomyography (SMG) sensors, or a combination of EMG, MMG and SMG sensors.

10. The system of claim 1, wherein the one or more wearable components consists of a single wearable component, and wherein all of the plurality of sensors are arranged on the single wearable component configured to be worn on or around a body part of the user.

11. The system of claim 1, wherein at least one of the one or more wearable components comprises a flexible or elastic band configured to be worn around a body part of the user.

12. The system of claim 11, wherein the flexible or elastic band comprises an armband configured to be worn around an arm of the user.

13. The system of claim 1, wherein the plurality of sensors further includes at least one Inertial Measurement Unit (IMU) sensor configured to continuously record IMU signals, wherein the processor-executable instructions, when executed by the at least one computer hardware processor, cause the at least one computer hardware processor to perform:
    providing the IMU signals and/or information based on the IMU signals as inputs to the first control mapping.

14. The system of claim 13, wherein the at least one IMU sensor and the plurality of neuromuscular sensors are arranged on a same wearable component.

15. The system of claim 1, wherein updating the first control mapping further comprises updating the first control mapping using the first control mapping output.

16. The system of claim 1, wherein the intention model is generated based on heuristic or intuitive approximation of user interactions with the device or observed user interactions by one or more users with the device.

17. The system of claim 1, wherein the device comprises a computer executing a user-interactive application, and wherein the operation of the device comprises an operation of the user-interactive application.

18. The system of claim 1, wherein the processor-executable instructions that, when executed by the at least one computer hardware processor, cause the at least one computer hardware processor to perform:
controlling the device using the second control mapping.

19. A method of adapting a control mapping associating sensor signals with control signals for controlling an operation of a device, the method comprises;
- obtaining a plurality of sensor signals from a plurality of sensors including a plurality of neuromuscular sensors arranged on one or more wearable components, wherein the plurality of neuromuscular sensors are configured to continuously record neuromuscular signals from a user;
- obtaining first state information for an operation of the device, wherein the first state information includes information relating to the state of a task;
- providing the first state information as input to an intention model associated with the operation of the device and obtaining a first intention model output including an estimate of an intended control signal;
- providing the neuromuscular signals and/or signals derived from the neuromuscular signals as inputs to a first control mapping and obtaining a first control mapping output;
- updating the first control mapping using the inputs provided to the first control mapping and the first intention model output to obtain a second control mapping, wherein the second control mapping is based at least in part on a comparison between the first control mapping output and the first intention model output, and
- controlling the device using a control signal based on the second control mapping.

20. A non-transitory computer-readable storage medium encoded with a plurality of instructions that, when executed by at least one computer hardware processor perform a method comprising:
- obtaining a plurality of sensor signals from a plurality of sensors including a plurality of neuromuscular sensors arranged on one or more wearable components, wherein the plurality of neuromuscular sensors are configured to continuously record neuromuscular signals from a user;
- obtaining first state information for an operation of a device, wherein the first state information includes information relating to the state of a task;
- providing the first state information as input to an intention model associated with the operation of the device and obtaining a first intention model output including an estimate of an intended control signal;
- providing the neuromuscular signals and/or signals derived from the neuromuscular signals as inputs to a first control mapping and obtaining a first control mapping output;
- updating the first control mapping using the inputs provided to the first control mapping and the first intention model output to obtain a second control mapping, and
- controlling the device using a control signal based on the second control mapping.

\* \* \* \* \*